(12) United States Patent
Silvestro

(10) Patent No.: US 11,617,857 B2
(45) Date of Patent: Apr. 4, 2023

(54) ENDOVASCULAR CATHETER WITH INTERNAL BALLOON

(71) Applicant: Medtronic Vascular, Inc., Santa Rosa, CA (US)

(72) Inventor: Claudio Silvestro, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 16/776,658

(22) Filed: Jan. 30, 2020

(65) Prior Publication Data

US 2021/0236774 A1    Aug. 5, 2021

(51) Int. Cl.
*A61M 25/01* (2006.01)
*A61M 25/09* (2006.01)

(52) U.S. Cl.
CPC .... *A61M 25/0125* (2013.01); *A61M 25/0147* (2013.01); *A61M 2025/09008* (2013.01)

(58) Field of Classification Search
CPC .......... A61M 2025/09008; A61M 2025/1045; A61M 2025/10; A61M 25/0662; A61M 2025/0681; A61M 2025/0079; A61M 2025/018; A61M 25/0125; A61M 25/0147; A61M 25/01; A61B 2017/22051
See application file for complete search history.

(56) References Cited

U.S. PATENT DOCUMENTS

| | | | | |
|---|---|---|---|---|
| 5,697,946 A | * | 12/1997 | Hopper | A61B 17/3421 606/185 |
| 5,792,118 A | * | 8/1998 | Kurth | A61M 25/0017 604/246 |
| 5,916,194 A | | 6/1999 | Jacobsen et al. | |
| 6,022,342 A | * | 2/2000 | Mukherjee | A61M 25/01 604/523 |
| 8,372,055 B2 | | 2/2013 | Thornton et al. | |
| 2001/0000041 A1 | * | 3/2001 | Selmon | A61B 17/3207 600/585 |
| 2002/0077651 A1 | | 6/2002 | Holmes, Jr. et al. | |
| 2002/0095141 A1 | * | 7/2002 | Belef | A61B 17/221 606/1 |
| 2004/0039371 A1 | * | 2/2004 | Tockman | A61M 25/0147 604/528 |
| 2005/0209673 A1 | | 9/2005 | Shaked | |
| 2006/0074398 A1 | * | 4/2006 | Whiting | A61M 25/0041 604/510 |
| 2008/0154172 A1 | | 6/2008 | Mauch | |

(Continued)

FOREIGN PATENT DOCUMENTS

WO    2019/066728 A1    4/2019

*Primary Examiner* — Tiffany Legette
(74) *Attorney, Agent, or Firm* — Brooks Kushman P.C.

(57) ABSTRACT

A catheter is disclosed that allows selective direction of a surgical tool into multiple blood vessels of a patient. The catheter includes a catheter body that has a main exit port and a side exit port. An internal balloon is provided within the catheter body. The internal balloon is inflatable, and can be located at or near a distal portion of the side exit port. When deflated, the internal balloon allows the surgical tool to advance past the side exit port and out the main exit port. When inflated, the internal balloon directs the surgical tool to advance out the side exit port instead of the main exit port.

20 Claims, 5 Drawing Sheets

(56) References Cited

U.S. PATENT DOCUMENTS

| | | | |
|---|---|---|---|
| 2011/0172698 A1* | 7/2011 | Davies, Jr. | A61M 25/104 606/194 |
| 2012/0232640 A1* | 9/2012 | Horvers | A61M 25/1029 623/1.11 |
| 2015/0165163 A1 | 6/2015 | Alvarez et al. | |

* cited by examiner

ENDOVASCULAR CATHETER WITH INTERNAL BALLOON

TECHNICAL FIELD

The present disclosure relates to endovascular catheters for percutaneous endovascular procedures, and more specifically to such endovascular catheters with an internal inflatable balloon to help guide catheter components and surgical tools within blood vessels of a patient.

BACKGROUND

The use of percutaneous endovascular procedures has been established as a minimally invasive technique to deliver a variety of clinical treatments in a patient's vasculature. As the application of endovascularly-delivered devices extends to new and more complex treatments, the anatomical configurations of the target vasculature can become more complex. Delivery of treatment to highly tortuous anatomical districts can be challenging.

SUMMARY

In one embodiment, an endovascular catheter includes an elongated and hollow catheter body extending along a longitudinal axis between a proximal end and a distal end, the distal end defining a main exit port of the catheter body, and the catheter body defining a side exit port located between the proximal end and the distal end, the catheter body configured to receive an elongated element to pass therethrough along the longitudinal axis. The endovascular catheter also includes an inflatable element disposed within the catheter body, wherein the inflatable element is configured to inflate at a location adjacent to the side exit port to direct the elongated element through the side exit port.

In another embodiment, an endovascular catheter includes an elongated and hollow catheter body configured to guide a guide a surgical tool into a desired vasculature, the catheter body extending along a longitudinal axis between a proximal end and a distal end, the distal end defining a main exit port of the catheter body, and the catheter body defining a side exit port located between the proximal end and the distal end. The endovascular catheter also includes an internal balloon disposed within the catheter body. The endovascular catheter is configured to operate in a first mode in which the internal balloon is deflated and the surgical tool is directed to exit the catheter body at the main exit port, and a second mode in which the internal balloon is inflated to direct the surgical tool to exit the catheter body at the side exit port.

In another embodiment, A method of selectively directing a surgical tool within a catheter is provided. The method includes inserting a catheter body into a vessel of a patient, the catheter body having a proximal end and a distal end, the distal end defining a main exit port of the catheter body, and the catheter body defining a side exit port located between the proximal end and the distal end of the catheter body, the side exit port having a proximal edge and a distal edge. The method further includes inflating an internal balloon at a location between the proximal edge of the side exit port and the distal end of the catheter body. The method further includes, after the step of inflating, advancing the surgical tool through the catheter body such that the inflated internal balloon directs the surgical tool to exit the catheter body through the side exit port

BRIEF DESCRIPTION OF THE DRAWINGS

FIG. 1A shows an internal balloon in a deflated state with a guide wire exiting a main exit port. FIG. 1B shows the internal balloon in an inflated state with the guide wire contacting the internal balloon. FIG. 1C shows the internal balloon forcing advancement of the guide wire to cause the guide wire to exit a side exit port.

DETAILED DESCRIPTION

Figure 1A:
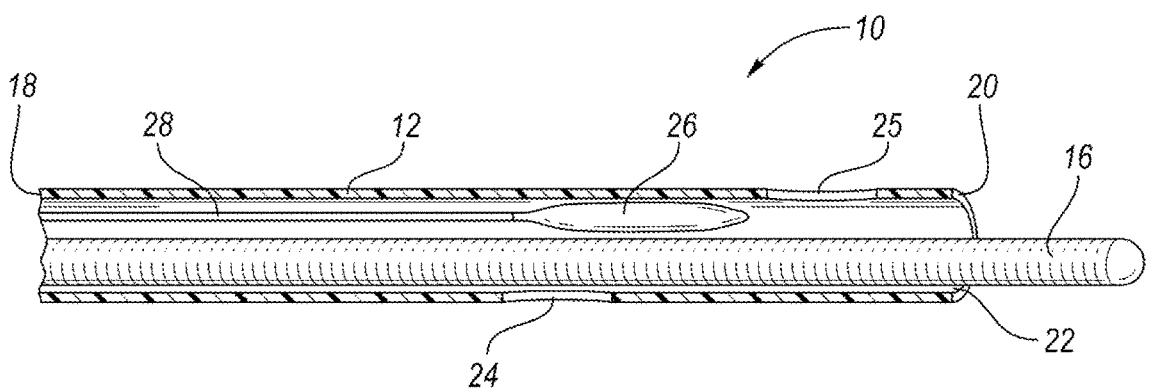
FIGS. 1A-1C are internal views of a catheter, with an outer catheter body shown in cross-section to reveal inner components thereof, according to embodiments.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis. The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" can refer to positions distant from or in a direction away from the clinician, while "proximal" and "proximally" can refer to positions near or in a direction toward the clinician. For the stent-graft prosthesis, "proximal" is the portion nearer the heart by way of blood flow path while "distal" is the portion of the stent-graft further from the heart by way of blood flow path.

The use of percutaneous endovascular procedures has been established as a minimally invasive technique to deliver a variety of clinical treatments in a patient's vasculature. As the application of endovascularly-delivered devices extends to new and more complex treatments, the anatomical configurations of the target vasculature can become more complex. Treatment of highly tortuous and challenging anatomical districts becomes increasingly frequent. Percutaneous endovascular devices such as catheters are typically tracked inside the patient's anatomy over a guide wire, which is a low-profile flexible wire used to guide the catheter into the blood vessels. Being able to properly place the guide wire into the desired anatomical district of the patient's vasculature is important to percutaneous endovascular procedures. Placement of the guide wire must therefore be performed in a time-efficient, reliable way to facilitate the procedure and guarantee access to the target anatomy.

This disclosure is generally directed to an endovascular catheter configured for use with percutaneous endovascular procedures. The catheter is designed so to be used for engagement and treatment of highly tortuous, anatomically complex districts of the patient's vasculature. The catheter is configured to allow treatment of several vascular areas via one single device. To do so, according to various embodiments including those described below, the catheter includes an outer catheter body having multiple exit ports aligned with corresponding regions of the patient's vasculature (e.g., corresponding arteries). A guide wire can be inserted into a first portion of the patient's vasculature, and the catheter body can slide along the guide wire into place. An inflatable element, such as a balloon, can be inserted into the catheter body and inflated therein to create an obstruction within the catheter body. Once the balloon is inflated, a medical device (or the guide wire, retracted) can subsequently be inserted into the catheter body, and the obstruction created by the inflated balloon directs the medical device into a desired exit port. This enables treatment of tight-angle bifurcations and challenging anatomies within the patient's vasculature.

Figure 1B:
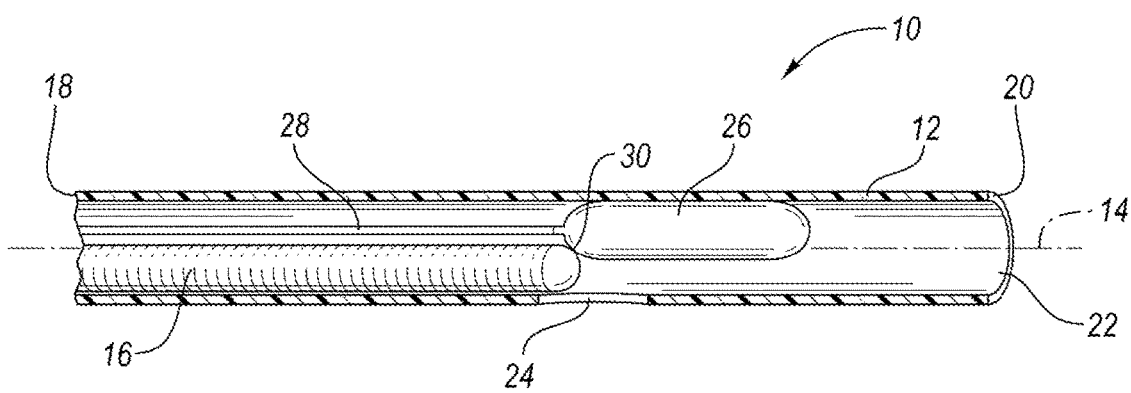
Figure 1C:
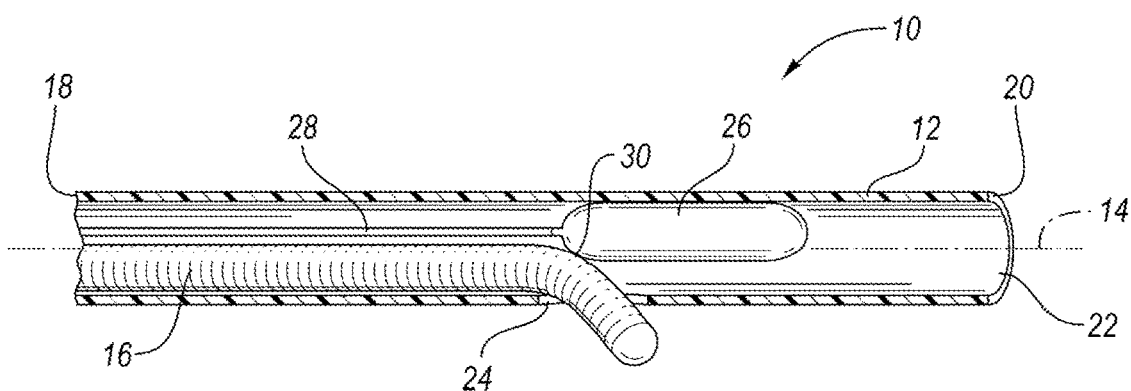

FIGS. 1A-1C illustrate an endovascular catheter 10 according to one embodiment. The catheter 10 includes an outer catheter body 12 (also referred to as a catheter guide wire lumen) that is generally elongated, hollow, and tubular (e.g., cylindrical) for use with percutaneous endovascular procedures, and for enabling various components and tools to be inserted therethrough. The catheter body 12 is shown here extending along a longitudinal axis 14 in a straight line, but is flexible such that the catheter body may bend and flex while being inserted into the patient's body. In one embodiment, the catheter body 12 is made of a braided or woven metallic or synthetic material to enable such flexibility.

A guide wire 16 is also provided. In application, the guide wire 16 may be inserted into the patient's vasculature until it reaches a desired location, and then the catheter body 12 is subsequently slid and guided along the guide wire 16 to the desired location.

The catheter body 12 extends along the longitudinal axis 14 between a proximal end 18 (e.g., closer to the operator) and a distal end 20 (e.g., the leading end of the catheter body 12 inserted into the patient's vasculature). The distal end 20 includes or defines a main exit port 22. The main exit port 22 is an aperture, opening, or the like that allows surgical tools that are internal to the catheter body 12 (e.g., the guide wire 16) to pass therethrough. As such, the diameter of the main exit port 22 may be larger than the diameter of each of the surgical tools within the catheter body 12. The main exit port 22 is coaxially-oriented to the longitudinal axis 14. In other words, a central axis extending through the main exit port 22 may be coaxial or parallel to the longitudinal axis 14.

The catheter body 12 also includes a side exit port 24. In at least one embodiment, the side exit port 24 is near or adjacent the distal end 20. For example, the distance between the side exit port 24 and the distal end 20 may be less than 25% of the distance between the proximal end 18 and the distal end 20, and in more particular embodiments, the distance between the side exit port 24 and the distal end 20 may be about 10% of the distance between the proximal end 18 and the distal end 20. When the catheter body 12 is guided to the desired location along the guide wire 16, the side exit port 24 may be aligned with a corresponding arterial branch (or other such branch in the vasculature), as illustrated in FIG. 1B, for example. This allows a surgical tool within the catheter body 12 to exit the side exit port 24 and into the arterial branch. A plurality of side exit ports may be included, allowing any number of side exit ports to be aligned with a corresponding number of arterial branches. A plurality of side exit ports may also be included to provide various options for placement of the catheter body 12, allowing the operator to choose one of a plurality of side exit ports to align with the desired arterial branch. The plurality of side exit ports may include two or more side exit ports that are axially in the same location but spaced circumferentially (equally or unequally). Alternatively, the plurality of side exit ports may be spaced axially and may be circumferentially aligned or unaligned. In other embodiments, any combination of the above multiple exit ports may be utilized. FIG. 1A depicts side exit port 24 and side exit port 25.

The catheter 10 also includes an inflatable member such as an internal balloon 26. The internal balloon 26 is configured to selectively inflate and deflate within the catheter body 12. The internal balloon 26 is carried on and coupled to an internal balloon inflation lumen 28. The internal balloon inflation lumen 28 is hollow, and extends through the proximal end 18 of the catheter body 12. In operation, the operator may pump or otherwise force fluid (e.g., saline solution liquid) through the internal balloon inflation lumen 28 and into the internal balloon 26, thereby inflating the internal balloon 26. Likewise, the operator may release or draw the fluid from the internal balloon 26 via the internal balloon inflation lumen 28 to deflate the internal balloon 26.

FIG. 1A shows the internal balloon 26 in a deflated state. When deflated, the internal balloon 26 maintains a low profile inside the catheter body 12, thus allowing relative movement between the guide wire 16 and the catheter body 12. With the low profile, the guide wire 16 can pass entirely through the distal end 20 of the catheter body 12, passing beyond the internal balloon 26 without obstruction. The internal balloon 26 can be positioned within the catheter body 12 at a location that aligns with at least a portion of the side exit port. In one embodiment, a portion of the internal balloon 26 overlaps with a portion of the side exit port 24 along the axis 14. This is shown in FIGS. 1A-1C. The internal balloon 26 can be fixed or otherwise coupled to the catheter body 12 such that the internal balloon 26 moves along with the catheter body 12 as it is inserted. This can assure that the internal balloon 26 remains at the proper position relative to the side exit port 24 for when it is desired to be inflated. And, the internal balloon 26 can be fixed at a location radially opposite from the side exit port 24 such that it inflates in a direction toward the side exit port. Alternatively, the internal balloon 26 may be moveable within the catheter body 12, allowing the operator to feed and advance the internal balloon 26 and the internal balloon inflation lumen 28 within the catheter body 12 once the catheter body 12 is properly located.

FIG. 1B shows the internal balloon 26 in an inflated state. Prior to inflation, the guide wire 16 can be retracted toward the proximal end 18 of the catheter body 12. This yields space for the internal balloon 26 to be inflated. The internal balloon 26 is dimensioned such that, when inflated, it obstructs the guide wire 16, thus preventing the guide wire 16 from passing beyond the internal balloon 26 and towards the distal end 20 of the catheter body 12. To provide a proper obstruction for the guide wire 16, the internal balloon 26 need not be inflated such that it filled the entire interior diameter of the catheter body 12. For example, in one embodiment, the inner diameter of the catheter body 12 is between 0.8 millimeters (mm) and 1.4 mm, such as 1.1 mm, the outer diameter of the internal balloon 26 when inflated is between 0.8 mm and 1.2 mm, such as 1.0 mm, and the outer diameter of the guide wire 16 is between 0.3 mm and 0.7 mm, such as 0.5 mm.

FIG. 1C shows the internal balloon 26 remaining in the inflated state. The guide wire 16 is now advanced by the operator. The guide wire 16 is obstructed by the internal balloon 26, and thus is forced to exit the side exit port 24 and into the arterial branch. In one embodiment, the distal end of the guide wire 16 contacts the internal balloon 26, and further advancement of the guide wire 16 forces the guide wire 16 to bend against the internal balloon 26 toward the direction of the side exit port 24. As such, the internal balloon 26 may be provided with a curved, angled or tapered edge 30 that is angled toward the side exit port 24 to assist in guiding the guide wire 16 to the side exit port 24.

While only one internal balloon 26 is shown in FIGS. 1A-1C, it should be understood that multiple internal balloons 26 can be utilized in an embodiment in which multiple corresponding side exit ports 24 are provided on the catheter body. For example, if the particular procedure requires a navigation through—or implantation within—multiple branches in the patient's vasculature, the catheter may be provided with multiple internal balloons 26 to help direct the surgical tool(s) into the multiple branches. In one embodiment, after inflation of the internal balloon 26, the guide wire 16 is directed through side exit port 24, whereupon other surgical devices can be guided. After direction of those surgical devices through the side exit port 24, the guide wire 16 can once again be retracted, and another internal balloon closer to the proximal end 18 can be inflated. Once that internal balloon is inflated, the guide wire can be directed into yet another side exit port aligned with that internal balloon, in which more surgical devices can be guided through via the guide wire 16. In other embodiments, multiple guide wires are utilized rather than retracting the same guide wire 16 back through each side exit port.

The internal balloon 26 may comprise an outer shell or structure that is impervious to surgical tools such as needles or guide wires. This can assure that the contact made by the surgical tool and the inflated internal balloon 26 does not puncture the internal balloon 26. The internal balloon can comprise, for example, a braided metallic or synthetic structure with gaps in the braids that are smaller than the diameter of the surgical tool. The braided nature of the material also provides flexibility, enabling the internal balloon 26 to inflate and deflate To prevent kinking or misdirection of the guide wire 16 as it contacts the internal balloon 26, at least a portion of the internal balloon 26 can be adhered (e.g., glued) to the inner wall of the catheter body 12, at a location radially opposite of the side exit port 24. In one embodiment, roughly one third to one half of the outer circumference of the internal balloon is adhered to the inner wall of the catheter body 12. As the internal balloon 26 is inflated, the adhered portion of the internal balloon remains in contact with the inner wall of the catheter body, and the non-adhered portion of the internal balloon expands radially outward toward the side exit port 24. This assures that as the guide wire 16 is extended, it is forced between the internal balloon 26 and the side exit port 24, eventually causing the guide wire 16 to exit the side exit port 24 while reducing the chance for a misdirection.

The internal balloon inflation lumen 28 can also be adhered (e.g., glued) to the inner wall of the catheter body 12. This prevents the internal balloon inflation lumen 28 from getting tangled with another lumen or guide wire within the catheter 10.

By using the catheter with an internal balloon as described herein, this allows the operator to selectively engage different anatomies via a single device. This also offers the possibility to engage different vascular branches simultaneously, keeping a more versatile design and keeping access to the main vessel while also treating the branched vessel. For example, a first device (e.g., guide wire 16) may be extended through the main exit port 22 into the main vessel while the internal balloon 26 is deflated. Then, while the first device is still extended into the main exit port 22, the internal balloon 26 can be inflated to obstruct the passageway within the catheter body 12. When a second device (e.g., another guide wire, stent, lumen, balloon, etc.) is advanced within the catheter body 12, the inflated internal balloon 26 can direct the second device into the side exit port 24 and into the branched vessel. This allows access to the main vessel through the main exit port 22 and simultaneous treatment in the branched, secondary vessel via the side exit port 24.

Figure 2:
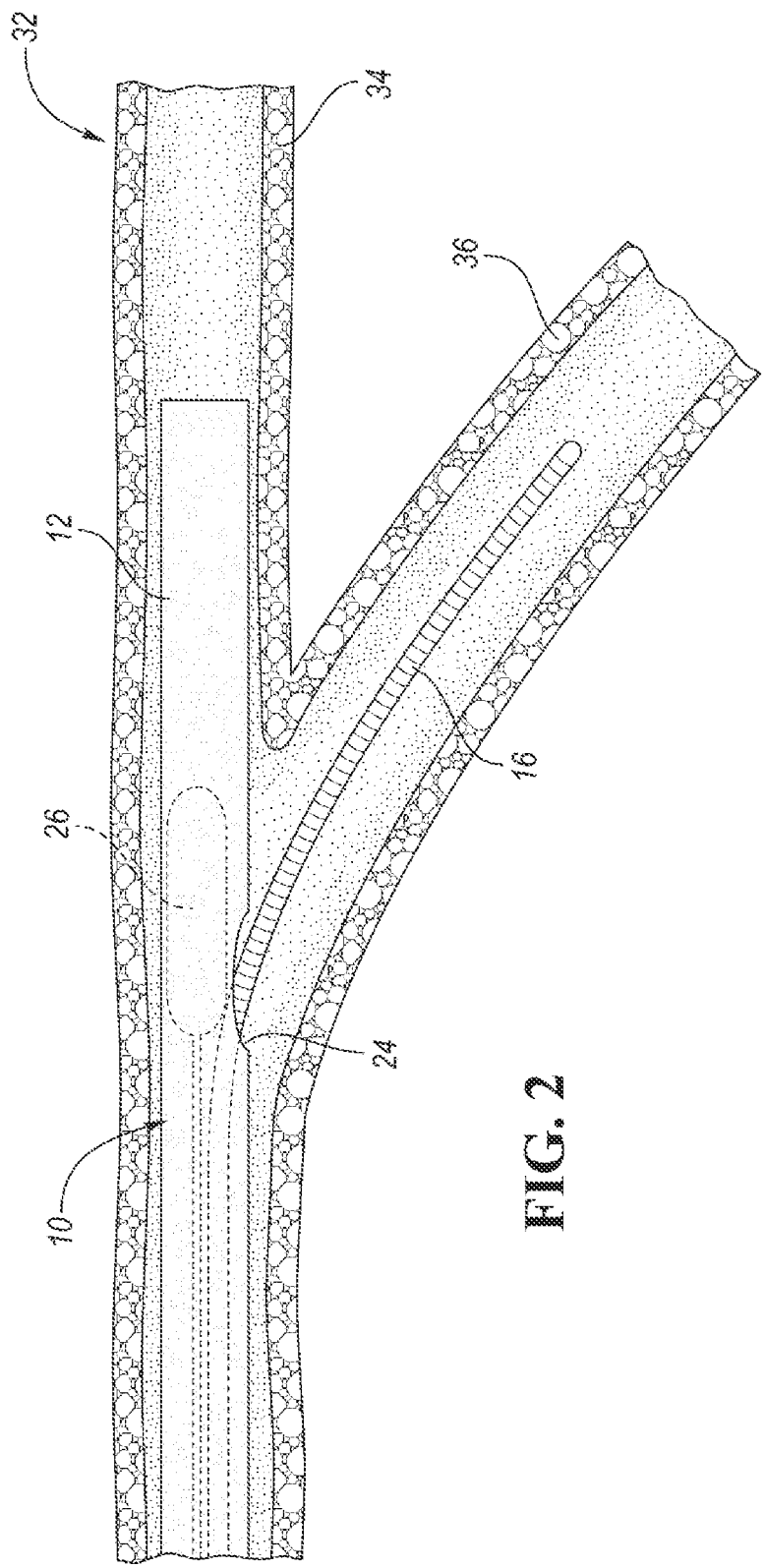
FIG. 2 is a cross-sectional view of a branched portion of a vasculature of a patient, with the catheter body disposed along a main artery and the guide wire extended into a secondary artery, according to one embodiment.

FIG. 2 shows the catheter 10 within positioned within a portion of the vasculature 32 of a patient. The catheter body 12 extends along a main vessel (e.g., artery) 34. The side exit port 24 is aligned with an opening into a branched or secondary vessel (e.g., artery) 36. When the internal balloon 26 is in its deflated state, the guide wire 16 is able to bypass the secondary vessel and extend through the distal end 20 of the catheter body 12 and into the main vessel 34. When the guide wire is partially retracted within the catheter body 12 and the internal balloon 26 is then inflated, the guide wire 16 will only be allowed to exit the side exit port 24. This allows access for other surgical devices (e.g., stents, etc.) to be guided along the guide wire 16 and into the branched vessel 36.

While FIG. 2 illustrates the surgical tool as a guide wire, it should be understood that the surgical tool being guided through the vasculature by the internal balloon is not limited to a guide wire. In other embodiments, the surgical tool is a needle, a lumen, a catheter, or other tools typically inserted via catheters.

Figure 3:
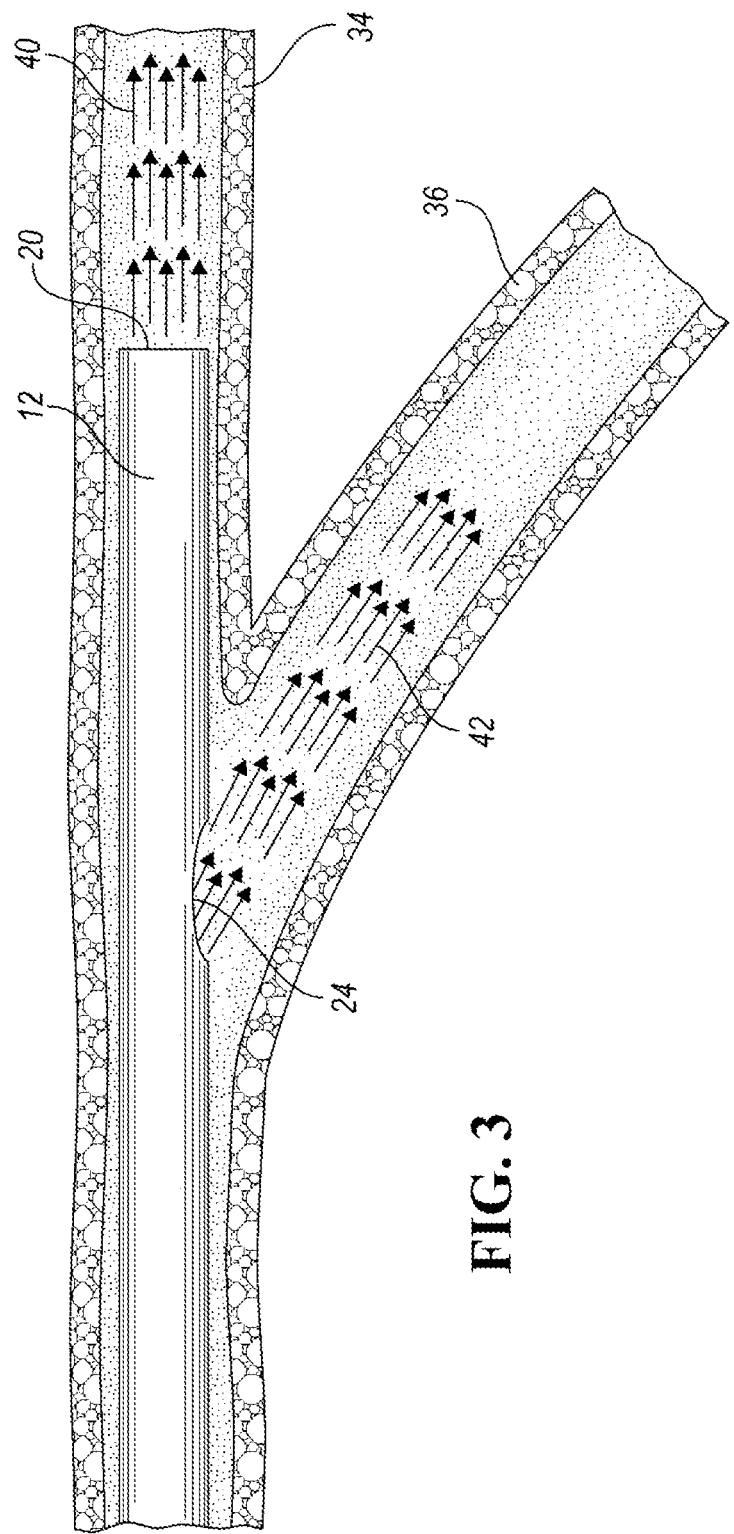
FIG. 3 is a cross-sectional view of a branched portion of the vasculature with the catheter directing a fluid, such as a fluid contrast medium, according to one embodiment.

In an embodiment illustrated in FIG. 3, the surgical tool is a liquid, such as contrast medium. The liquid contrast medium can be a liquid dye or contrast configured to improve viewable pictures of the inside of the patient's body produced by x-rays, computed tomography (CT), magnetic resonance (MR) imaging, ultrasound, and the like. The catheter body 12 may once again house the internal balloon (not shown) therein. The internal balloon may selectively inflate or deflate to direct the liquid contrast medium into either the main vessel 34 or the secondary vessel 36. When the internal balloon is deflated, the liquid contrast medium may be directed into the main vessel 34, as represented by arrows 40. When the internal balloon is inflated, at least a portion of the liquid contrast medium may be directed into the secondary vessel 36, as represented by the arrows 42.

In this embodiment in which the surgical tool is a liquid contrast medium, the internal balloon may be sized such that, when inflated, the internal balloon contacts and seals off the entire inner wall of the catheter body 12. This prevents substantially all of the liquid contrast medium from traveling into the main vessel 34 and instead directs substantially all of the liquid contrast medium to travel into the secondary vessel 36. In one embodiment, the outer diameter of the internal balloon when inflated outside of the catheter body 12 is greater than the inner diameter of the catheter body 12, but is held to an outer diameter that is equivalent to the inner diameter of the catheter body 12 when inside the catheter body.

Figure 4:
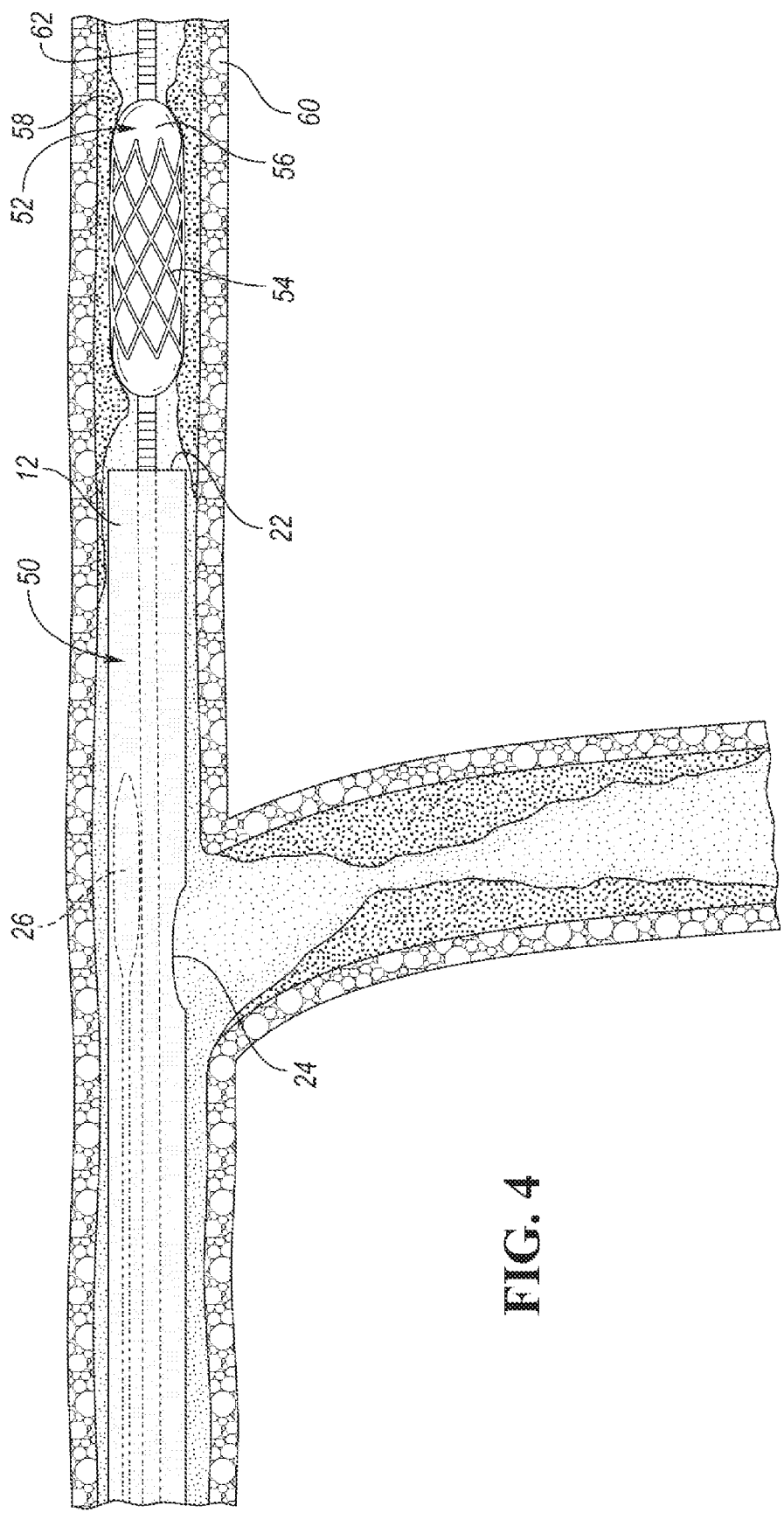
FIG. 4 is a cross-sectional view of a branched portion of the vasculature, with a catheter body located in a main vessel and an internal balloon deflated to allow a balloon stent to pass into a main vessel, according to one embodiment.
Figure 5:
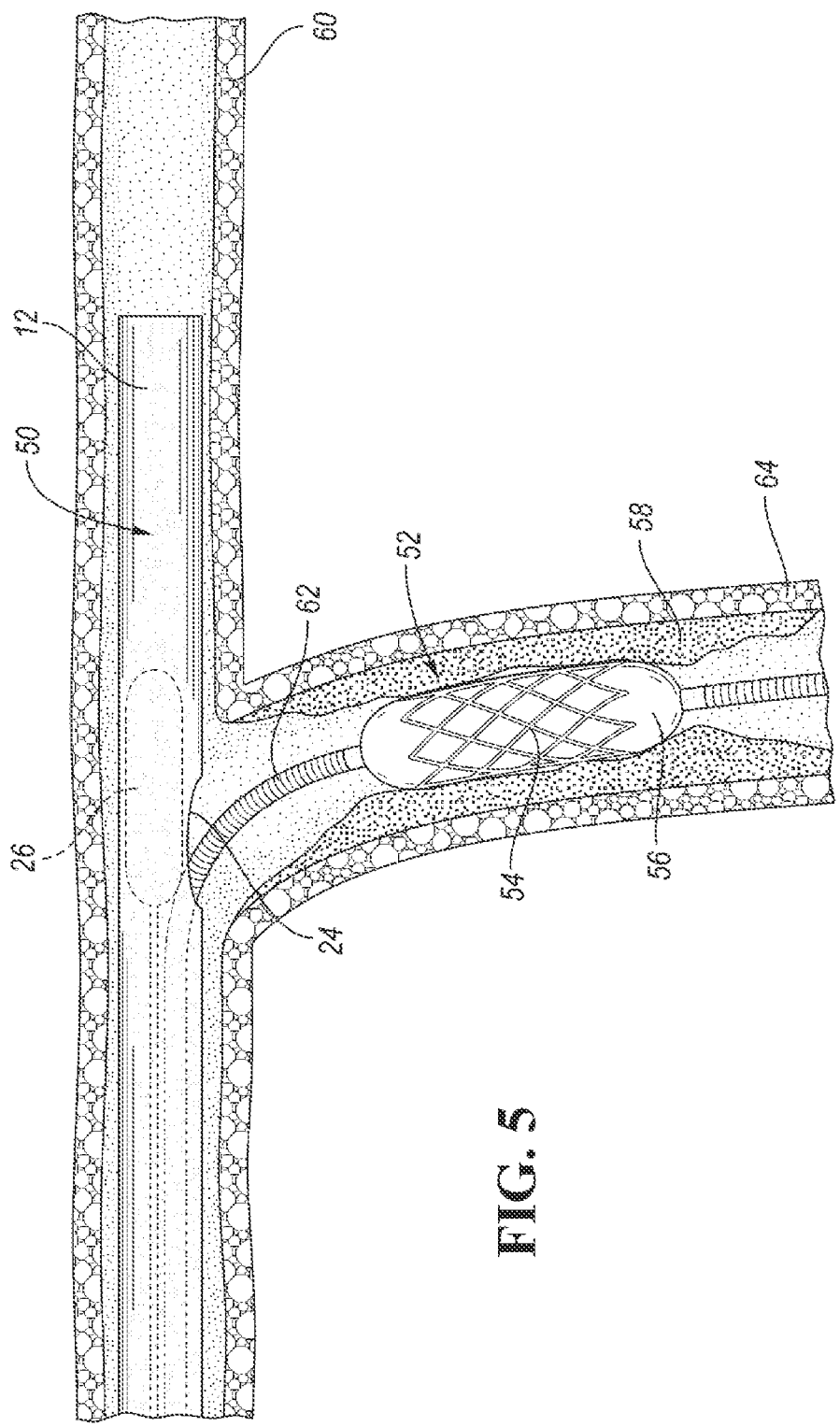
FIG. 5 is a cross-sectional view of the branched portion of the vasculature of FIG. 4, with the catheter body disposed in the main vessel and the internal balloon inflated to direct the balloon stent to pass into a secondary vessel, according to one embodiment.

In other embodiments, the surgical tool is a stent, such as a balloon stent. This is shown in FIGS. 4-5. Referring to FIG. 4, a catheter 50 includes a catheter body 12 and an inflatable internal balloon 26, similar to previous embodiments. The catheter 50 is used for delivery of a balloon stent 52 within the vasculature of the patient. In a surgical procedure involving a balloon stent, a stent 54 along with an inflatable balloon 56 are delivered with or through the catheter body 12, and extended axially out therefrom to a desired location. The stent 54 may be a small mesh tube made of medical-grade metal (e.g., stainless steel, cobalt alloy). The stent 54 can be initially delivered in a contracted or constricted position, and then expanded via the inflatable balloon 56, which can inflate with a slightly-pressurized liquid such as a saline solution. When the balloon 56 is inflated to radially expand the stent 54, the balloon 56 pushes back plaque or buildup 58 on the walls of the artery. The balloon 56 is then deflated and removed, and the stent 54 is left attached to the patient's artery to help keep the blood vessel open.

FIG. 4 shows the balloon stent 52 located in a main artery 60 via a dedicated guide wire or lumen 62. The balloon 56 is shown in a semi-inflated position, beginning to make contact with and push back the buildup 58 in the main artery 60. The internal balloon 26 is deflated to allow the balloon stent 52 to travel out of the main exit port 22 of the catheter body 12 and into the main artery 60.

FIG. 5 shows the balloon stent 52 located in a secondary artery 64. To direct the balloon stent 52 into the secondary artery 64, the internal balloon 26 was inflated prior to the balloon stent 52 being extended out of the catheter body 12. With the internal balloon 26 inflated, a forced extension of the lumen 62 forces the balloon stent 52 to exit the side exit port 24 of the catheter body 12, and travel into the secondary artery 64. Once advanced into the secondary artery 64, the balloon 56 is inflated (shown partially inflated in FIG. 5) to push against the buildup 58 in the secondary artery 64. The balloon 56 can be deflated and retracted through the side exit port 24, leaving behind the stent 54 attached to the secondary artery 64.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. An endovascular catheter comprising:
    an elongated and hollow catheter body extending along a longitudinal axis between a proximal end and a distal end, the distal end defining a main exit port of the catheter body, and the catheter body defining a side exit port located between the proximal end and the distal end, the catheter body configured to receive an elongated element to pass therethrough along the longitudinal axis;
    an internal inflation lumen having a proximal end and a distal end; and
    an elongated, inflatable element carried on the distal end of the internal inflation lumen and disposed within the catheter body, the inflatable element is configured to inflate to an inflation state at a location adjacent to the side exit port to direct the elongated element through the side exit port, and the internal inflation lumen movable within the catheter body along the longitudinal axis without directly contacting the catheter body.

2. The endovascular catheter of claim 1, wherein the elongated, inflatable element includes an outermost, cylindrical region having a circumference, the inflatable element in the inflation state has an inflation diameter less than an inner diameter of the catheter body to form a gap between an inner surface of the catheter body and the circumference of the outermost, cylindrical region of the inflatable element.

3. The endovascular catheter of claim 1, wherein the catheter body defines a second side exit port located between the proximal end and the distal end.

4. The endovascular catheter of claim 1, wherein inflatable element comprises a braided metallic or synthetic structure defining gaps smaller in diameter than the elongated element.

5. The endovascular catheter of claim 1, wherein when the inflatable element is in a deflated state, the elongated element is enabled to pass longitudinally beyond the inflatable element and out the main exit port.

6. The endovascular catheter of claim 5, wherein when the inflatable element is in the inflated state, the elongated element is forced to exit the catheter body through the side exit port via contact with the inflatable element.

7. An endovascular catheter comprising:
    an elongated and hollow catheter body configured to guide a surgical tool into a vasculature, the catheter body extending along a longitudinal axis between a proximal end and a distal end, the distal end defining a main exit port of the catheter body, and the catheter body defining a side exit port located between the proximal end and the distal end;
    an internal inflation lumen having a proximal end and a distal end, the internal inflation lumen movable within the catheter body along the longitudinal axis without directly contacting the catheter body; and a cylindrically-shaped internal balloon carried on the distal end of the internal inflation lumen and disposed within the catheter body, the cylindrically-shaped internal balloon at least partially adhered to an inner wall of the catheter body to form an adherence region;

wherein the endovascular catheter is configured to operate in:

a first mode in which the internal balloon is deflated and the surgical tool is directed to exit the catheter body at the main exit port, and a second mode in which the internal balloon is inflated to direct the surgical tool to exit the catheter body at the side exit port.

8. The endovascular catheter of claim 7, wherein the surgical tool is a liquid contrast medium.

9. The endovascular catheter of claim 7, wherein the surgical tool is a balloon catheter disposed within the catheter body and moveable along the longitudinal axis relative to the catheter body.

10. The endovascular catheter of claim 7, wherein when the endovascular catheter is operating in the second mode, a second surgical tool is extending through the main exit port.

11. The endovascular catheter of claim 7, wherein the cylindrically-shaped internal balloon includes an outermost, cylindrical region having a circumference, and the adherence region is one third to one half of the circumference of the outermost, cylindrical region of the cylindrically shaped internal balloon.

12. The endovascular catheter of claim 7, wherein the surgical tool is a guide wire disposed within the catheter body and moveable along the longitudinal axis relative to the catheter body.

13. The endovascular catheter of claim 12, wherein when the endovascular catheter is in the second mode, the guide wire contacts the inflated internal balloon and bends toward the side exit port.

14. A method of selectively directing a surgical tool within a catheter, the method comprising:

inserting a catheter body into a vessel of a patient, the catheter body having a proximal end and a distal end, the distal end defining a main exit port of the catheter body, and the catheter body defining a side exit port located between the proximal end and the distal end of the catheter body, the side exit port having a proximal edge and a distal edge;

after the inserting step, advancing an internal balloon carried on a distal end of an internal inflation lumen within the catheter body to a location where a proximalmost end of the internal balloon is between the proximal and distal edges of the side exit port;

inflating the internal balloon at the location to an inflation state after the advancing step; and while the internal balloon is in the inflation state, advancing the surgical tool through the catheter body such that the inflated internal balloon directs the surgical tool to exit the catheter body through the side exit port.

15. The method of claim 14, wherein the surgical tool is a liquid contrast medium.

16. The method of claim 14, wherein the catheter body has an upper inner wall region and a lower inner wall region opposing the upper inner wall region, and the outer diameter of the internal balloon contacting the upper inner wall region and not contacting the lower inner wall region when in the inflation state.

17. The method of claim 14, wherein the surgical tool is a guide wire, and the method further comprises:

before the step of inflating, inserting the guide wire through the main exit port of the catheter body; and subsequently retracting the guide wire to pass over the distal edge of the side exit port, wherein the step of inflating occurs after the step of retracting.

18. The method of claim 17, further comprising:

while the internal balloon is in the inflation state, extending the guide wire wherein the inflated internal balloon directs the guide wire through the side exit port.

19. The method of claim 14, wherein the surgical tool is an internal balloon catheter.

20. The method of claim 19, further comprising inflating a balloon of the internal balloon catheter after the step of inflating the internal balloon.

* * * * *